United States Patent [19]

Babler

[11] 3,994,953

[45] Nov. 30, 1976

[54] ETHYL Z- AND E-2-VINYL-2-METHYLCY-CLOBUTANECARBOXYLATE

[76] Inventor: James H. Babler, 125 Callan, Evanston, Ill. 60202

[22] Filed: Oct. 25, 1974

[21] Appl. No.: 517,814

[52] U.S. Cl. .................. 260/468 H; 260/486 H; 260/488 H; 260/593 H; 260/617 R; 260/633
[51] Int. Cl.$^2$ ......................................... C07C 69/74
[58] Field of Search .................... 260/468 H, 617 R

[56] References Cited
OTHER PUBLICATIONS

Tumlinson et al., J. Org. Chem., 36, pp. 2616–2621 (1971).

Primary Examiner—Lorraine A. Weinberger
Assistant Examiner—Michael Shippen
Attorney, Agent, or Firm—John J. McDonnell

[57] ABSTRACT

The present invention is concerned with a method for preparing grandisol, the major component of the boll weevil sex pheromone. This method involves the conversion of 4-chloro-2-butanone to 5-chloro-3-methyl-1-penten-3-ol, acid-catalyzed isomerization of the latter compound to E- and Z-5-chloro-3-methyl-2-penten-1-ol, followed by conversion to ethyl 3-[2-chloroethyl]-3-methyl-4-pentenoate by treatment with triethyl orthoacetate, cyclization of ethyl 3-[2-chloroethyl]-3-methyl-4-pentenoate to ethyl Z- and E-2-vinyl-2-methylcyclobutanecarboxylate by reaction with base, conversion of ethyl Z- and E-2-vinyl-2-methylcyclobutanecarboxylate to Z- and E-2-[2-methyl-2-vinylcyclobutyl]-2-propanol by reaction with methyllithium, and the conversion of the latter compound to grandisol by reaction with diborane and basic hydrogen peroxide followed by dehydration.

1 Claim, No Drawings

ETHYL Z- AND E-2-VINYL-2-METHYLCYCLOBUTANECARBOXYLATE

The present invention is concerned with the preparation of grandisol, 1, the major component of the boll weevil sex pheromone.

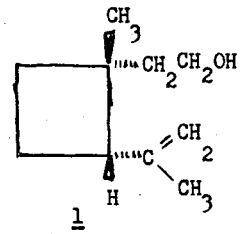

1

It is an object of the present invention to provide a method for the inexpensive preparation of grandisol which is amenable to industrial scale production.

In accordance with the object of the present invention, a method for preparing grandisol is set out in Scheme I.

Scheme I

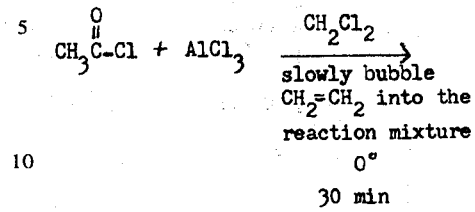

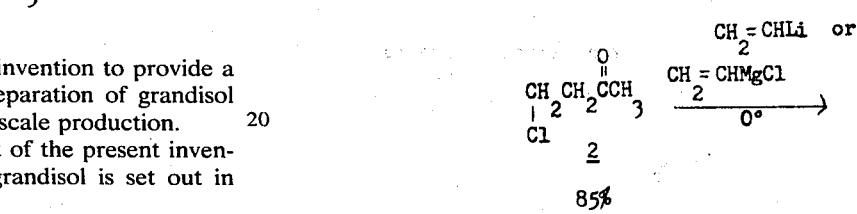

2

85%

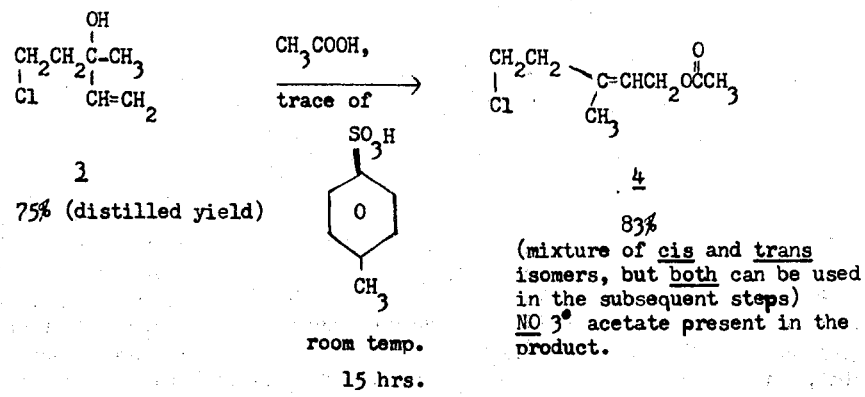

3

75% (distilled yield)

4

83%
(mixture of cis and trans isomers, but both can be used in the subsequent steps)
NO 3° acetate present in the product.

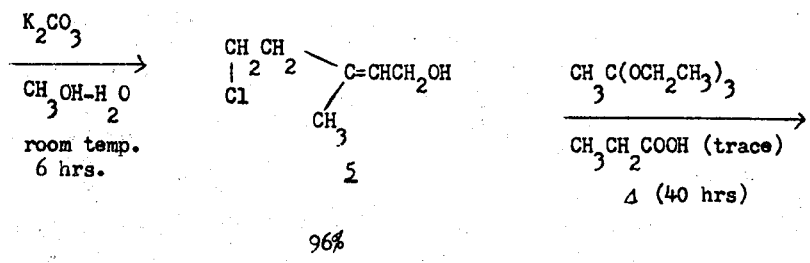

5

96%

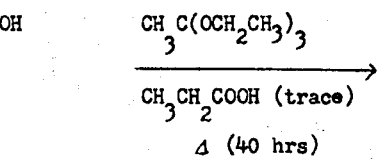

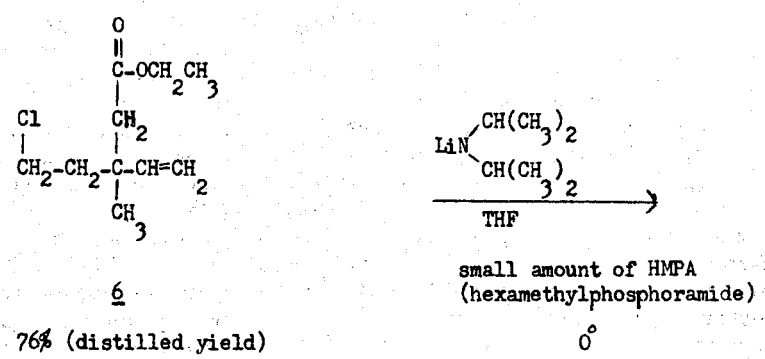

6

76% (distilled yield)

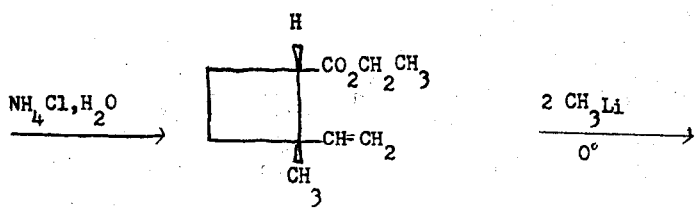

(predominant stereoisomer)

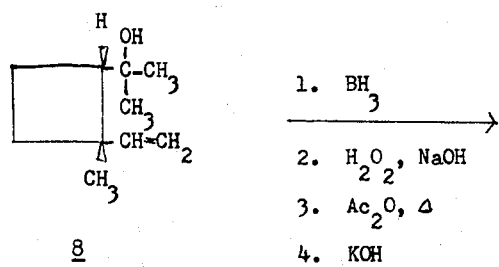

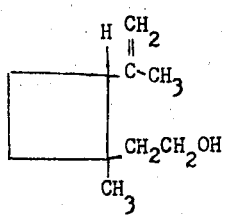

Compound 8, Z-2-[2-methyl-2-vinylcyclobutyl]-2-propanol and its conversion to grandisol (1) is described in J. Org. Chem., 36, 2616 (1971). 5-Chloro-3-methyl-1-penten-3-ol (compound 3), 5-chloro-3-methyl-2-penten-1-ol (compound 5), ethyl 3-[2-chloroethyl]-3-methyl-4-pentenoate (compound 6), and ethyl Z- and E- 2-vinyl-2-methylcyclobutanecarboxylate (compound 7) represent novel intermediates in the present process.

Those skilled in the chemical arts will recognize the interchangeability of a variety of reactants. Thus vinyllithium can be replaced by vinylmagnesium halide, preferably vinylmagnesium chloride, or the sequence of acetylide addition followed by catalytic reduction can be used to achieve an equivalent chemical transformation.

The present invention comprehends a method for the preparation of grandisol of the type terminating with the conversion of 2-[2-methyl-2-vinylcyclobutyl]-2-propanol to grandisol, the improvement which comprises the sequential preparation of 4-chloro-2-butanone, 5-chloro-3-methyl-1-penten-3-ol, 5-chloro-3-methyl-2-penten-1-ol, ethyl 3-[2-chloroethyl]-3-methyl-4-pentenoate, and ethyl 2-vinyl-2-methylcyclobutanecarboxylate, and the conversion of ethyl 2-vinyl-2-methyl-cyclobutanecarboxylate to 2-[2-methyl-2-vinylcyclobutyl]-2-propanol. It also comprehends a method for the preparation of ethyl Z- and E-2-vinyl-2-methylcyclobutanecarboxylate, an intermediate in the synthesis of grandisol, comprising the steps of:

a. converting 4-chloro-2-butanone to 5-chloro-3-methyl-1-penten-3-ol by reaction with vinyllithium or vinylmagnesium chloride;

b. converting 5-chloro-3-methyl-1-penten-3-ol to 5-chloro-3-methyl-2-penten-1-ol by acid-catalyzed rearrangement followed by basic hydrolysis;

c. converting 5-chloro-3-methyl-2-penten-1-ol to ethyl 3-[2-chloroethyl]-3-methyl-4-pentenoate by reacting 5-chloro-3-methyl-2-penten-1-ol with triethyl orthoacetate in the presence of acid;

d. converting ethyl 3-[2-chloroethyl]-3-methyl-4-pentenoate to ethyl Z- and E- 2-vinyl-2-methylcyclobutanecarboxylate by reacting ethyl 3-[2-chloroethyl]-3-methyl-4-pentenoate with diisopropylamine anion or a comparable strongly basic amine anion followed by rapid quenching;

e. converting ethyl Z- and E-2-vinyl-2-methylcyclobutanecarboxylate to Z- and E- 2-[2-methyl-2-vinylcyclobutyl]-2-propanol by reacting ethyl Z- and E-2-vinyl-2-methylcyclobutanecarboxylate with methyllithium or methylmagnesium halide.

The present invention further comprehends a method for preparing ethyl Z- and E-2-vinyl-2-methylcyclobutanecarboxylate comprising reacting ethyl 3-[2-chloroethyl]-3-methyl-4-pentenoate with diisopropylamine anion or comparable strongly basic amine anion followed by rapid quenching of the reaction in weak acid and for preparing the product produced by this method which is ethyl Z- and E- 2-vinyl-2-methylcyclobutanecarboxylate.

Insect sex attractants (pheromones) are of considerable interest and economic importance in that they offer a nontoxic ecologically acceptable method of surveying and controlling insect populations. The components of the pheromone emitted by the male boll weevil (Anthonomus grandis Boheman) are known to be terpenoids I, II, III, and IV. (Tumlinson, et al., Science 166, 1012, 1969).

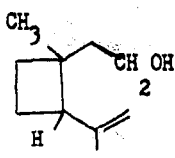

I

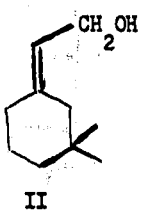

II

III

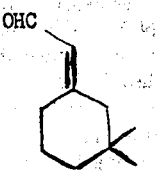

IV

Table 1, taken from Tumlinson (supra), indicates the effectiveness of various combination of I through IV in attracting female boll weevils as compared to the naturally occurring pheromone. Response of female boll weevils in laboratory bioassay to optimum concentrations of compounds I, II, III and IV. The T/S equals net response to test sample divided by net response to a standard. The sample in each case consisted of the compound or the indicated mixture of compounds in 0.2 ml. of dichloromethane. The standards used were live male boll weevils or steam distillates that were equivalent in attractancy to live males.

TABLE I

| Sample | Respective amounts ($\mu$g) | Average T/S |
|---|---|---|
| I | 0.09 | 0.11 |
| II | 0.07 | 0.06 |
| III | 0.12 | 0.00 |
| IV | 0.12 | 0.11 |

$$\begin{array}{c}ClCH_2CH_2 \\ \phantom{xx}\diagdown \\ \phantom{xxxx}C{=}C \\ \phantom{xx}\diagup \phantom{xxxx}\diagdown \\ CH_3 \phantom{xxxx} CH_2OCCH_3 \\ \phantom{xxxxxxxxx}\|\\ \phantom{xxxxxxxxx}O\end{array}$$

| | | |
|---|---|---|
| I, II | 0.09, 0.07 | 0.15 |
| I, III | 0.09, 0.12 | 0.06 |
| I, IV | 0.09, 0.12 | 0.12 |
| II, III | 0.07, 0.12 | 0.24 |
| II, IV | 0.07, 0.12 | 0.12 |
| III, IV | 0.12, 0.12 | 0.16 |
| I, II, III | 0.09, 0.07, 0.12 | 1.00 |
| I, II, IV | 0.09, 0.07, 0.12 | 0.84 |
| I, III, IV | 0.09, 0.12, 0.12 | 0.07 |

TABLE I-continued

| Sample | Respective amounts ($\mu$g) | Average T/S |
|---|---|---|
| II, III, IV | 0.07, 0.12, 0.12 | 0.18 |
| I, II, III, IV | 0.09, 0.07, 0.12, 0.12 | 1.26 |

The invention will appear more fully by the examples which follow. These examples are given by way of illustration only and are not to be construed as limiting the invention either in spirit or in scope, as many modifications both in materials and methods will be apparent to those skilled in the art. In these examples, temperatures are given in degrees centigrade (° C.) and quantities of materials are expressed in parts by weight unless otherwise specified. The relationship between parts by weight and parts by volume is the same as that existing between grams and milliliters.

EXAMPLE 1

In an inert atmosphere, 25.25 parts of 4-chloro-2-butanone in 50 parts by volume of anhydrous ethyl ether are added dropwise to a cold (0°) mixture of 110 parts by volume of a 2.5 M solution of vinyllithium in tetrahydrofuran and 200 parts by volume of anhydrous diethyl ether. After 15 minutes, 4 parts of water by volume are added dropwise to quench the reaction. The mixture is then poured into 300 parts by volume of brine, and the product is separated from the reaction mixture by extraction with ether. The ether extracts are washed with brine, then dried over anhydrous magnesium sulfate, and filtered. The ether is subsequently removed by evaporation at reduced pressure. Fractional distillation affords 23.7 parts (75% yield) of 5-chloro-3-methyl-1-penten-3-ol, bp: 85°–90° (50 mm).

EXAMPLE 2

To a solution of 9.52 parts of 5-chloro-3-methyl-1-penten-3-ol in 60 parts by volume of acetic acid and 12 parts by volume of acetic anhydride are added 0.9 parts of p-toluenesulfonic acid monohydrate. After 18 hours at room temperature, the solution is poured into 600 parts by volume of cold water and the product is isolated by pentane extraction. The pentane extracts are washed successively with saturated sodium bicarbonate, 10% sodium chloride solution, then dried over anhydrous magnesium sulfate and filtered. Removal of the pentane by evaporation at reduced pressure, followed by fractional distillation, affords 9.14 parts of a mixture of E- and Z-5-chloro-3-methyl-2-penten-1-ol acetate. The formulas are:

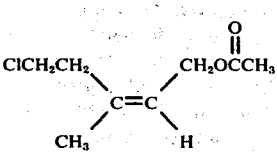

EXAMPLE 3

To a solution of 2.74 parts of a 2:1 mixture of E/Z stereoisomers of 5-chloro-3-methyl-2-penten-1-ol acetate in 24 parts by volume of methanol and 8 parts by volume of water are added 2.7 parts of anhydrous potassium carbonate. After being stirred for 7 hours at room temperature, 200 parts by volume of 10% sodium chloride solution is added and the product is isolated by ether extraction. The ether extracts are washed with brine, dried over anhydrous magnesium sulfate, and filtered. Removal of the ether by evaporation at reduced pressure yields 2.00 parts (96% yield) of a 2:1 mixture of E/Z stereoisomers of 5-chloro-3-methyl-2-penten-1-ol.

EXAMPLE 4

To a solution of 1.97 parts of a 2:1 mixture of E/Z stereoisomers of 5-chloro-3-methyl-2-penten-1-ol in 20 parts by volume of triethyl orthoacetate is added 0.14 part of propionic acid. This solution is heated for 40 hours in an oil bath (~150°) in such a manner that the ethanol that forms during the reaction is slowly distilled through a Vigreaux column. After cooling the solution, 20 parts by volume of pentane and 20 parts by volume of 1 M sulfuric acid are added, and this mixture is stirred vigorously for 5 minutes to hydrolyze the excess triethyl orthoacetate. The mixture is then diluted with 150 parts by volume of water and the product is isolated by pentane extraction. The pentane extracts are washed with saturated sodium bicarbonate, 10% sodium chloride solution, dried over anhydrous magnesium sulfate, and filtered. Removal of the pentane, followed by fractional distillation, yields 2.27 parts (76%) of ethyl 3-[2-chloroethyl]-3-methyl-4-pentenoate. The formula is:

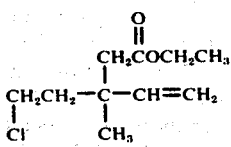

EXAMPLE 5

To a cold (−5° C) solution of 1.30 parts of diisopropylamine in 15 parts by volume of anhydrous tetrahydrofuran under an inert atmosphere is added dropwise slowly a mixture of 6.0 parts by volume of a 1.8 M solution of methyllithium in ether and 5 parts by volume of anhydrous tetrahydrofuran. After 15 minutes, a solution of 0.95 part of ethyl 3-[2-chloroethyl]-3-methyl-4-pentenoate in 10 parts by volume of anhydrous tetrahydrofuran and 1.0 part by volume of hexamethylphosphoramide is added dropwise slowly. After 20 minutes at −10° and 3 hours at 0°, the reaction is quenched by rapid addition of 5 parts by volume of saturated aqueous ammonium chloride. The mixture is then diluted with 180 parts by volume of water and the product is isolated by pentane extraction. The pentane extracts are washed successively with 5% hydrochloric acid, saturated sodium bicarbonate, and 10% sodium chloride solution. The pentane extracts are then dried over anhydrous magnesium sulfate and filtered. Removal of the pentane by evaporation is reduced pressure, followed by distillation, yields in a typical experiment a 65:35 mixture of ethyl Z and E-2-vinyl-2-methylcyclobutanecarboxylate. The major product is the Z-isomer, the one necessary for a stereo-selective synthesis of grandisol. The formulas are:

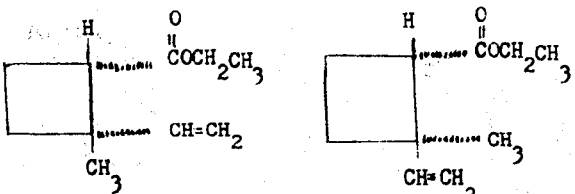

The Z-isomer has an nmr spectrum which is characterized by a 3 proton snglet at 1.34δ and a 2 proton quartet at 4.06δ. The corresponding E-isomer absorptions are, respectively, 1.13δ and 4.11δ.

NOTE: Hexamethylphosphoramide is not necessary for the success of this cyclization reaction; it does accelerate the rate of the reaction, however. The ratio of stereo isomers obtained varies with the reaction temperature, with very low reaction temperature (−70° C) favoring formation of the E-isomer.

EXAMPLE 6

To a cold (0°) mixture of 5 parts by volume of anhydrous ether and 10 parts by volume of a 1.8 M solution of methyllithium in ether is added a solution of 1 part of a 65:35 mixture of ethyl Z- and E-2-vinyl-2-methylcyclobutanecarboxylate in 5 parts by volume of anhydrous ether. After 90 minutes at 0°, the reaction is quenched by slow addition of 5 parts by volume of saturated ammonium chloride solution. After dilution with 30 parts by volume of water, the product is isolated by ether extraction. The ether extracts are washed with 10% sodium chloride solution, dried over anhydrous magnesium sulfate, and filtered. Removal of the ether by evaporation at reduced pressure affords in quantitative yield of 65:35 mixture of Z- and E-2-[2-methyl-2-vinylcyclobutyl]-2-propanol, whose spectral characteristics are identical to those previously reported for these stereoisomers. The formulas are:

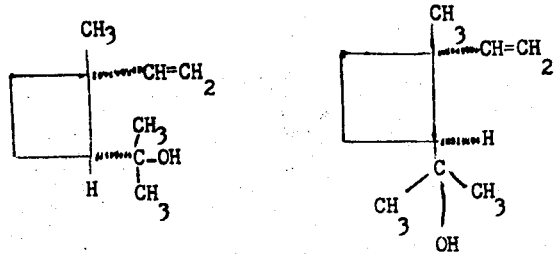

Literature reference:
J. H. Tumlinson, R. C. Gueldner, D. D. Hardee, A. C. Thompson, P. A. Hedin, and J. P. Minyard, J. Org. Chem., 36, 2616 (1971).

What is claimed is:
1. Ethyl Z- and E-2-vinyl-2-methylcyclobutanecarboxylate.

* * * * *